(12) United States Patent
Miller et al.

(10) Patent No.: US 10,363,087 B2
(45) Date of Patent: Jul. 30, 2019

(54) TISSUE RESECTION DEVICE

(75) Inventors: David Miller, Austin, TX (US); Todd Dalton, Austin, TX (US); Mitch Gilkey, Austin, TX (US)

(73) Assignee: Apollo Endosurgery US, Inc., Austin, TX (US)

( * ) Notice: Subject to any disclaimer, the term of this patent is extended or adjusted under 35 U.S.C. 154(b) by 1803 days.

(21) Appl. No.: 12/902,747

(22) Filed: Oct. 12, 2010

(65) Prior Publication Data

US 2011/0087222 A1    Apr. 14, 2011

Related U.S. Application Data

(60) Provisional application No. 61/250,869, filed on Oct. 12, 2009.

(51) Int. Cl.
*A61B 18/14*  (2006.01)

(52) U.S. Cl.
CPC .......... *A61B 18/14* (2013.01); *A61B 18/1445* (2013.01); *A61B 2018/144* (2013.01); *A61B 2018/1407* (2013.01)

(58) Field of Classification Search
CPC ...... A61B 2018/1407; A61B 2018/141; A61B 2018/144; A61B 18/14; A61B 18/1445; A61B 2017/00269; A61B 17/32056

USPC ...................................... 606/41, 45, 113, 47
See application file for complete search history.

(56) References Cited

U.S. PATENT DOCUMENTS

| | | | |
|---|---|---|---|
| 5,651,788 A | 7/1997 | Fleischer et al. | |
| 5,961,526 A | 10/1999 | Chu et al. | |
| 6,098,629 A | 8/2000 | Johnson et al. | |
| 6,500,176 B1 * | 12/2002 | Truckai | A61B 18/1445 |
| | | | 606/205 |
| 6,743,228 B2 | 6/2004 | Lee et al. | |
| 2005/0149099 A1 | 7/2005 | Yamano et al. | |
| 2006/0229600 A1 * | 10/2006 | Canady | 606/45 |
| 2008/0015575 A1 * | 1/2008 | Odom et al. | 606/51 |
| 2009/0018602 A1 | 1/2009 | Mitelberg et al. | |

FOREIGN PATENT DOCUMENTS

WO    WO02089655 A2    11/2002

\* cited by examiner

*Primary Examiner* — Michael F Peffley
*Assistant Examiner* — Samantha M Good
(74) *Attorney, Agent, or Firm* — Donald K. Jones

(57) ABSTRACT

Instruments and methods are provided for performing submucosal medical procedures in a desired area of the digestive tract using endoscopy. The instruments include a mucosal resection device, a tissue grasper and a snare. Systems include a combination of one or more of such instruments. Embodiments of various methods for performing the procedures are also provided.

18 Claims, 6 Drawing Sheets

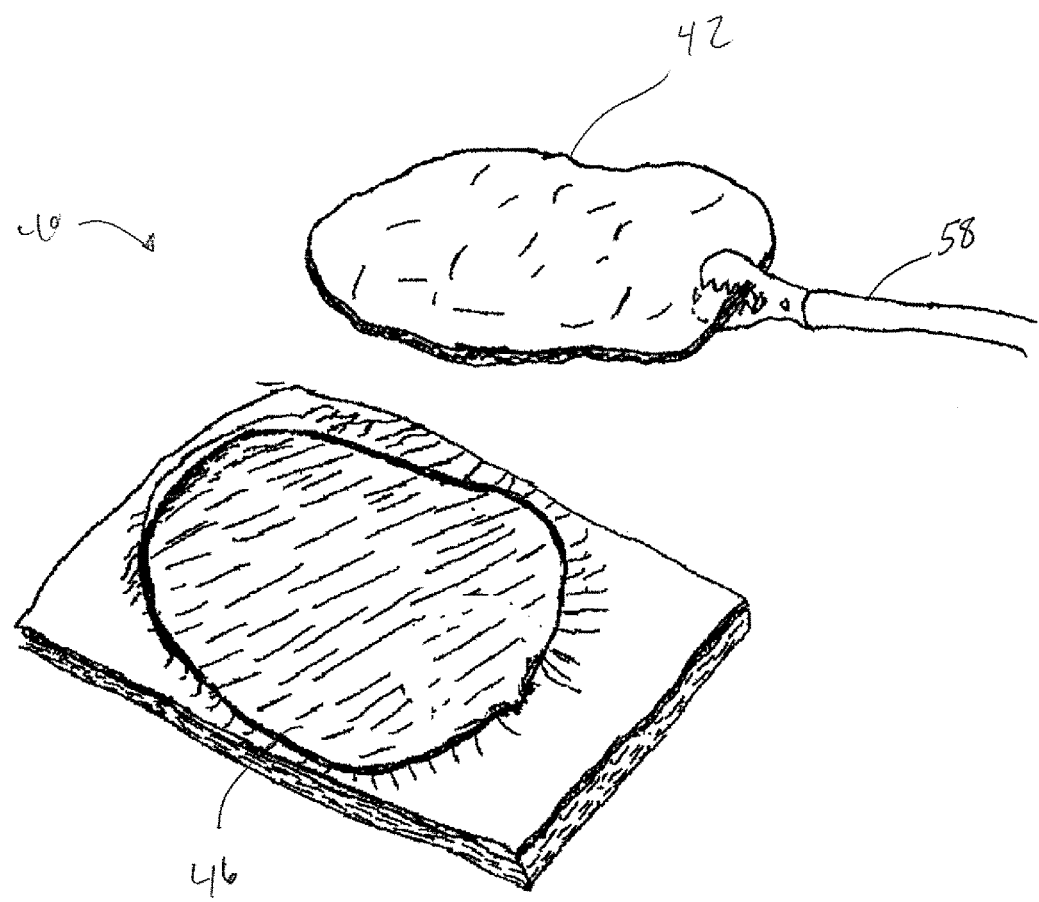

TISSUE RESECTION DEVICE

CROSS-REFERENCE TO RELATED APPLICATION

This application claims benefit of U.S. Provisional Application No. 61/250,869, filed Oct. 12, 2009, which is hereby incorporated by reference herein in its entirety.

FIELD OF THE INVENTION

The present invention relates to a mucosal resection device and a method for performing submucosal medical procedures in a desired area of the digestive tract using an endoscope.

BACKGROUND OF THE INVENTION

The field of gastrointestinal endoscopy has for many years focused on diagnostic and therapeutic techniques to observe, modify and remove tissues located in the digestive tract. General endoscopic procedural techniques such as visualizing, dilating, cutting and manipulating tissue have been accomplished using flexible devices such as endoscopes, balloons, snares and electrosurgical tools well known in the art.

While many of these devices and techniques have been useful in identifying and removing some neoplastic lesions of the mucosal layer as well as providing access to general locations within the digestive tract for the placement of submucosal implants, there are some lesions and areas of the digestive tract which are extremely difficult to resect or access. For example, the en bloc removal of large flat mucosal lesions presents numerous problems for current endoscopic tools and techniques. In addition, to effectively diagnosis some disorders (gastric motility, irritable bowel syndrome, chronic intestinal pseudo-obstruction, etc.) a biopsy of the muscular wall or the myenteric plexus may be necessary. Currently, access to these types of specimens requires full thickness biopsies which can be particularly difficult from an endoscopic approach requiring extremely skilled closure techniques.

There have been some advances in endoscopic techniques to resect flat lesions of the mucosal layer generally termed, Endoscopic Mucosal Resection (EMR). One of these EMR techniques, "lift and cut", involves the injection of saline or other biocompatible solution beneath the lesion in an attempt to raise the lesion thereby changing the geometry to make it suitable for resection using conventional snare devices.

Modifications to this technique are disclosed in U.S. Pat. No. 5,651,788 in which a lesion is identified and an injection catheter is used to inject saline to elevate the lesion. A ligator is attached to the distal end of the endoscope and suction is applied to the lesion to bring the tissue into the ligator. A ligator band is then applied to the tissue to form a banded mushroom-like polyp which is suitable for removal with an electrosurgical snare.

Alternatively U.S. Pat. No. 5,961,526 discloses a coaxial needle and severing snare assembly in which a needle is used to pierce tissue adjacent a target lesion to elevate the lesion with saline. Once the lesion is elevated, the needle is retracted from the tissue and the snare is extended from the needle lumen to surround the lesion. The lesion is then aspirated into an aspiration cylinder adjacent the distal end of the endoscope and the snare is cinched to sever the tissue surrounding the lesion.

While EMR techniques have been shown to be effective in treating some flat neoplastic lesions there are limitations and complications associated with these techniques. A major limitation associated with this technique is the size of the lesion that can be resected. Generally, these EMR techniques are suitable only for resecting mucosal lesions which are less than 2 cm in diameter. While larger or irregular shaped lesions may be resected in a piecemeal fashion, this is undesirable since small portions of the lesion may remain. Another limitation of these techniques includes uncertainty of the area being resected. Once tissue has been suctioned into a cap ligator or aspiration cylinder, the tissue is directly adjacent the visualization means of the endoscope obscuring the field of view. One complication associated with these EMR techniques is in relation to the use of the needle injection system. Manipulating the injection catheter to position the needle through the mucosal layer into the submucosal layer can ultimately result in puncturing the muscular wall of the digestive tract which may lead to infection or peritonitis. Another complication associated with EMR techniques is damage to the underlying muscular layer. Saline and other non-viscous fluids used to elevate the lesion dissipate relatively quickly after injection into the submucosal layer, such that portions of the underlying muscular layer may be included in the suctioned tissue and inadvertently damaged when using the electrosurgical tool for resection.

In order to overcome some of the size, irregular shapes and visualization limitations associated with EMR techniques, a new procedure called Endoscopic Submucosal Dissection (ESD) has been developed. With this procedure the periphery of the target resection area, which includes the lesion, is marked. An injection catheter is used to deliver a viscous fluid within the submucosal layer, which does not readily dissipate, throughout the target resection area. Once the target resection area has been elevated, an incision is made through the mucosal layer at the edge of the resection area using an electrosurgical needle knife. The physician uses the needle knife to cut the mucosal layer along the periphery of the target resection area. Once the boundary of the resection area has been cut, the physician then uses the needle knife to manually cut the submucosal connective tissue binding the mucosal layer to the muscular wall. Once the physician has completed the submucosal dissection, the mucosal layer is free to be removed in one piece. While this procedure allows the physician to resect large, irregular shaped lesions en bloc, it requires a high degree of skill on the part of the physician and is still subject to the complications associated with needle perforations and muscular layer injury.

In performing the ESD method of resecting a neoplastic lesion, as well as, performing a submucosal medical procedure it is apparent that dissecting the connective tissue of the submucosal space is an important step in having a successful outcome. Numerous investigators have attempted to provide ways of dissecting the submucosal connective tissue.

In U.S. Pat. No. 6,098,629 a method of implanting a submucosal esophageal bulking device is disclosed. The patent further discloses the use of a blunt dissecting member to create a submucosal pocket. In addition, the patent discloses the use of a balloon inserted into the submucosal layer to dissect the submucosal tissue when dilated to form a submucosal pocket.

In PCT Patent Application No. WO 02/089655, methods of implanting submucosal gastric implants are disclosed. The application further discloses various configurations of mechanical and electrosurgical dissection instruments for dissecting the connective tissue of the submucosal layer to form a submucosal pocket in which to place a gastric implant. Included in the description of mechanical dissection instruments are various configurations of balloon dissection instruments.

In U.S. Patent Application No. US2005/0149099, a submucosal dissection instrument, system and method are disclosed. The application further discloses an electrosurgical high frequency knife in combination with a submucosal dissection balloon. Included in the method are the steps of sequentially activating the high frequency knife to create a hole and advancing the balloon assembly into the hole with expansion of the balloon dissecting the connective tissue of the submucosal layer. These steps of the method are repeated until all of the connective tissue beneath the lesion is completely dissected.

With most of the aforementioned disclosed submucosal dissection techniques the physician is required to initially advance a significant portion of a dissection instrument into the submucosal layer while the connective tissue is generally intact. These techniques require that a pushing force be transmitted to the tip of the instrument to dissect the submucosal connective tissue. During application of this pushing force there is a risk that the tip of the instrument may injure or perforate the muscular wall or the mucosal layer.

In performing the disclosed method using the electrosurgical high frequency knife the initial hole through the mucosal layer may be visualized endoscopically. Once the balloon assembly is advanced into the submucosal incision hole and expanded to create a cavity, further advancement of the high frequency knife to form a second hole must be conducted without visualization. During the second hole formation and subsequent holes, without visual confirmation of the orientation of the high frequency knife there is a risk of perforating the muscular wall or mucosal layer.

SUMMARY OF THE INVENTION

In accordance with one aspect of the present invention there is provided a mucosal layer tissue resection device for removing a target area of mucosal tissue in the digestive tract of a mammal. The mucosal layer tissue resection device includes a tubular shaft having proximal and distal ends and a lumen extending therethrough. Located at the distal end of the shaft are first and second elongated tubular tissue guides which are formed of a nonconductive material and biased outwardly. Each tubular tissue guide has an elongated slot through the wall which extends longitudinally along at least a portion of the guide length. The slots of the tissue guides are positioned opposing each other. An electrosurgical loop cutter having an elongate electroconductive member slidably positioned within the lumen of the tubular shaft and a distal wire portion formed into a loop. The distal wire portion forms a loop which is partially positioned in the lumen of the first tissue guide, then extends generally perpendicular through the slot of the first tissue guide to the slot and lumen of the second tissue guide terminating back at the elongate electroconductive member. The proximal end of the shaft is coupled to a handle assembly having a slide assembly. The slide assembly is coupled to the proximal end of the elongate electroconductive member and includes an electrosurgical connector to electrically couple an electrosurgical generator to the loop cutter. The slide assembly of the handle allows the electrosurgical loop cutter to be advanced distally or retracted proximally.

In accordance with another aspect of the present invention the electrosurgical loop cutter of the resection devices includes first and second electrically insulated tubular wire guides. The tubular wire guides are coupled to the elongated member forming a "Y" configuration. The cutting wire extends through the lumen of the first and second wire guides which are slidably positioned within the lumens of the first and second tubular tissue guides, respectively. The wire guides each have an outer diameter which is larger than the width of the slots in the tissue guides, thereby preventing movement of the wire guides through the slots.

In accordance with yet another aspect of the present invention there is provided first and second tubular tissue guides in which the first tissue guide has a longer length than the second tissue guide.

In accordance with still another aspect of the present invention the tubular tissue guides have an arcuate shape. The arcuate shape of the tissue guide may generally lay within a plane which is generally parallel to the plane of the tissue to be resected.

In accordance with yet another aspect of the present invention there is provided a method for performing a submucosal medical procedure in which a target area of mucosal tissue is resected using a mucosal layer resection device. The method includes the step of forming a large mucosal layer dissected area in the digestive tract of a mammal defining a target area to be resected. The method also includes the step of providing a mucosal layer resection device. The method additionally includes the step of inserting the distal section of a first tissue guide through an opening in the mucosal layer into the submucosal space beneath the target area to be resected and a second tissue guide above the target area to be resected. The method additionally also includes the step of positioning the distal section of the resection device to define a path along the submucosal boundary of the target area. The method further includes the step of operating the mucosal layer resection device to move the elongate electroconductive member distally thereby causing the electrosurgical cutter to move distally along the path defined by the tissue guides thus resecting the target area of mucosal tissue from the surrounding mucosal tissue. The method additionally further includes the step removing the mucosal layer resection device from the mammal.

BRIEF DESCRIPTION OF THE DRAWINGS

FIGS. 4B and 4C are perspective views showing a method of resecting a desired region of mucosal tissue according to an embodiment of the present invention.

DETAILED DESCRIPTION OF THE INVENTION

Figure 1:
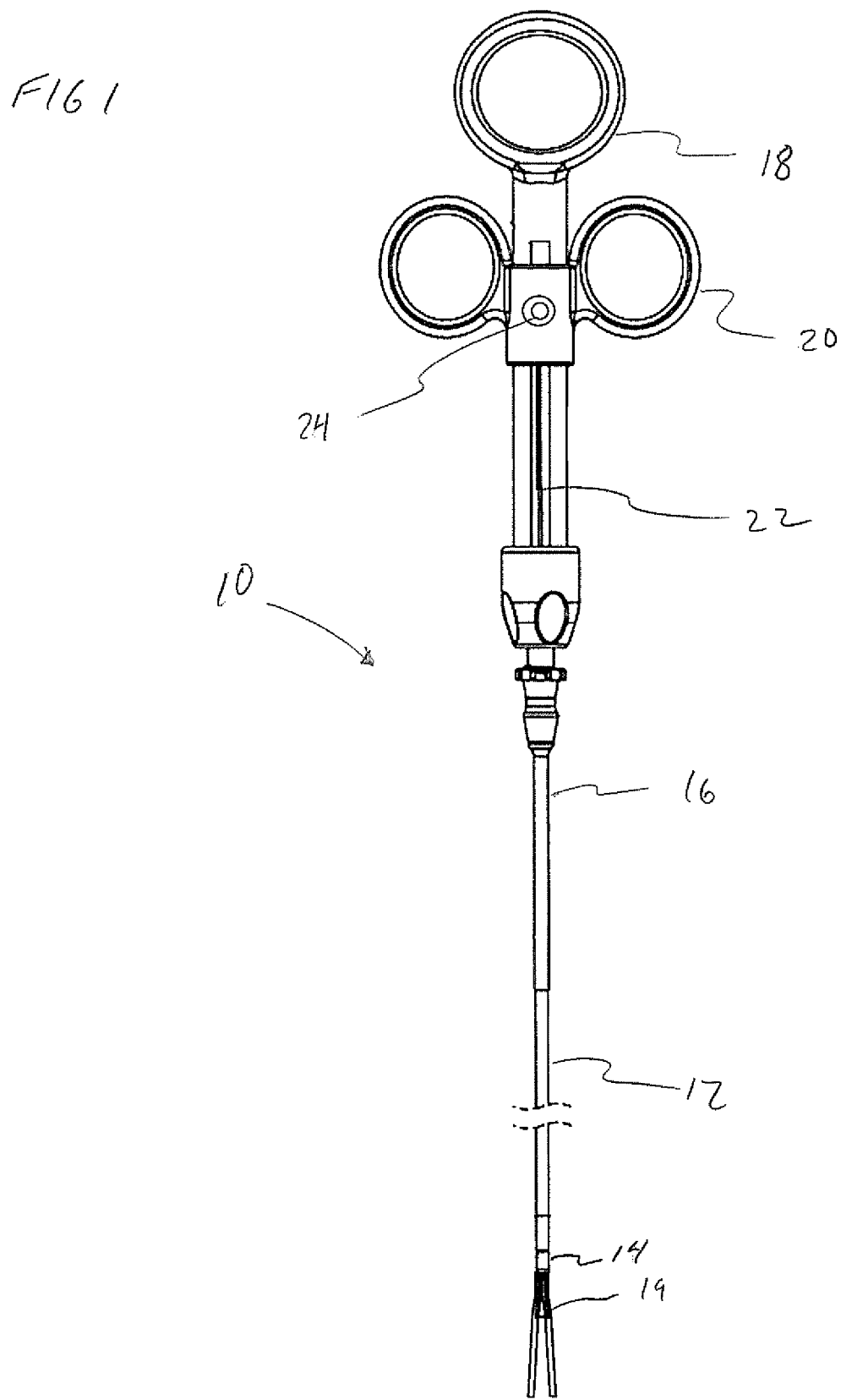
FIG. 1 is a side view of a tissue resection device according to an embodiment of the present invention.

FIG. 1 illustrates a tissue resection device for performing a submucosal medical procedure to resect a portion of the mucosal layer in the digestive tract of a mammal according to an embodiment of the present invention. The tissue resection device 10 includes an elongate catheter 12 having a distal end 14, a proximal end 16 and a lumen extending therethrough. Handle assembly 18 is coupled to the proximal end 16 of catheter 12 and electrosurgical loop cutter wire 19 is positioned at the distal end. Handle assembly 18 includes a slide assembly 20 which is fixedly coupled to the proximal end of the cutting wire actuator 22 of the electrosurgical loop cutter wire 19. Slide assembly 20 includes an electrical connector 24 which is in electrical contact with proximal end 22 and facilitates the coupling of an electrosurgical generator to supply energy to cutter wire 19.

Figure 2A:
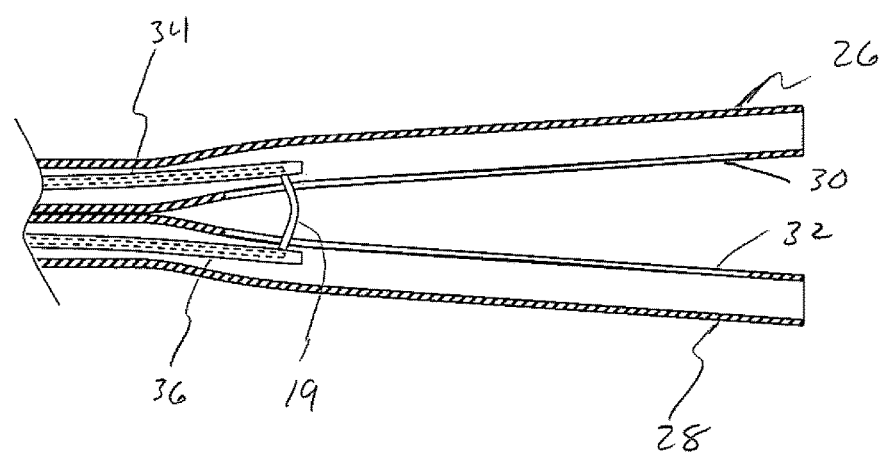
FIG. 2A is an enlarged partial cross-sectional view of the distal end of a tissue resection device in a first position according to an embodiment of the present invention.
Figure 2B:
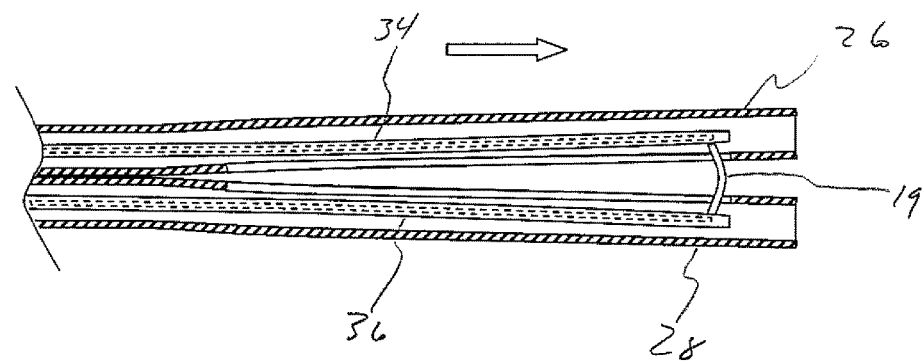
FIG. 2B is an enlarged partial cross-sectional view of the distal end of a tissue resection device in a second position according to an embodiment of the present invention.

FIGS. 2A and 2B illustrate the distal end of tissue resection device 10 in more detail showing a partial cross section of elongate first and second tubular tissue guides 26 and 28 respectively. Each of the tubular tissue guides are biased outwardly. As shown the first and second tubular tissue guides also each have a longitudinally extending slot, 30 and 32 respectively, extending through the wall. Loop cutter wire 19 extends through the slots of the tissue guides and portions of the loop cutter wire 19 positioned within the lumens of the tissue guides are supported by tubular wire guides 34 and 36, respectively. Referring to FIGS. 1, 2A and 2B, the proximal ends of wire guides 34 and 36 and loop 19 are fixedly coupled to cutting wire actuator 22 forming a "Y" configuration (not shown). When the handle slide assembly 20 is moved distally the cutting wire actuator 22 causes the wire guides 34 and 36 along with loop cutter wire 19 to move distally. The loop cutter wire 19 advances distally along a path defined by the slots 30 and 32 in the first and second tissue guides 26 and 28.

Figure 3A:
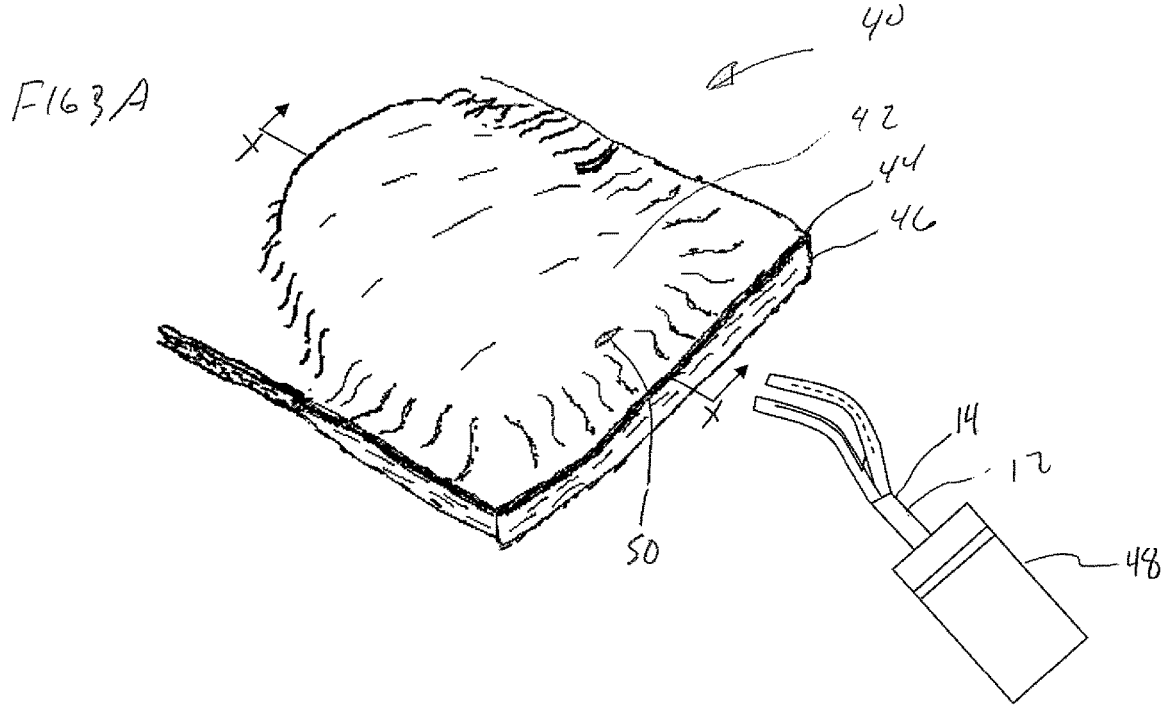
FIG. 3A is a perspective view of a portion of the digestive tract in which a tissue resection device is positioned adjacent a desired region of mucosal tissue which has previously been dissected.
Figure 3B:
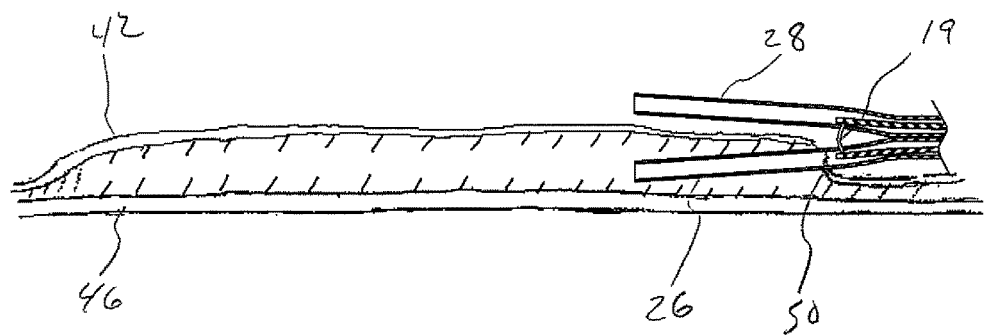
FIGS. 3B through 3E are cross-sectional views, taken along X-X of FIG. 3A, showing a method of resecting a large portion of a desired region of mucosal tissue using a mucosal resection device according to an embodiment of the present invention.
Figure 3C:
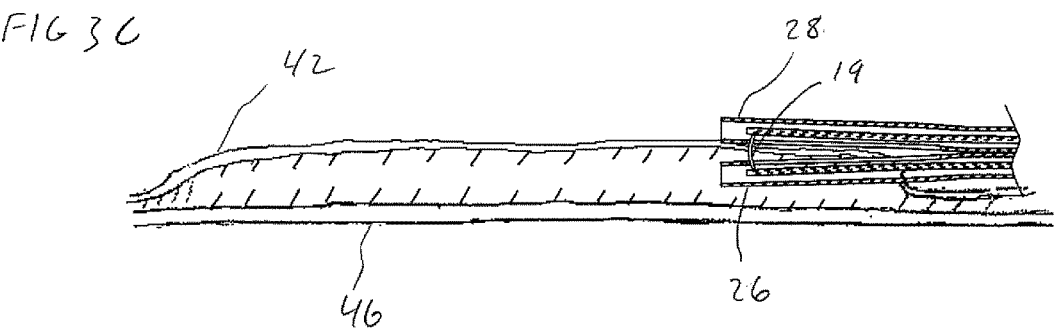
Figure 3D:
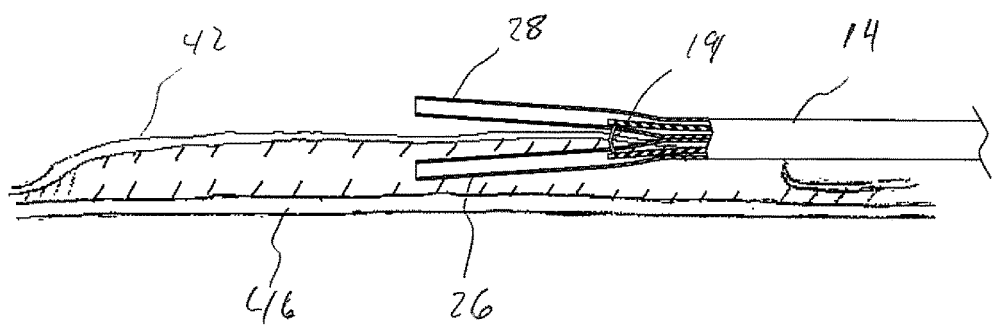
Figure 3E:
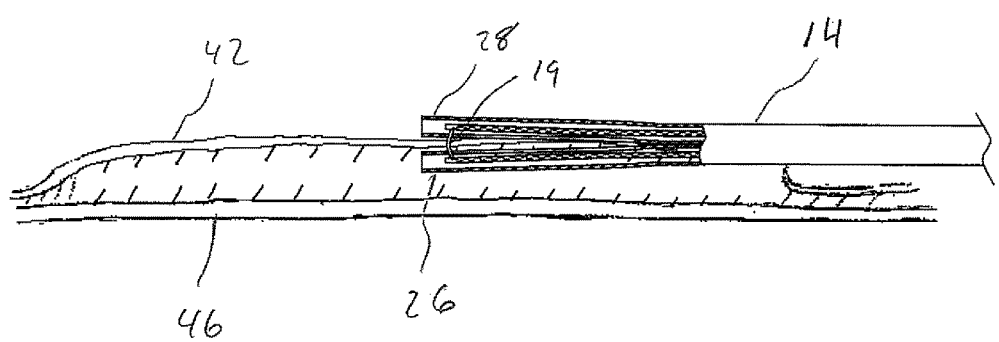

FIG. 3A shows a perspective view of a portion of the digestive tract 40 having a desired region of previously dissected mucosal tissue 42, un-dissected mucosal tissue 44 and the underlying muscle layer 46, using methods and described in US Patent Application Publication No: US 2009/0018602 A1 entitled "METHODS AND SYSTEMS FOR PERFORMING SUBMUCOSAL MEDICAL PROCEDURES" to Mitelberg, et al. and assigned to the same assignee as the present invention and herein incorporated in its entirety by reference. Also shown in this figure is an endoscope 48 positioning the distal end 14 of catheter 12 of tissue resection device 10 adjacent a mucosal opening 50.

FIGS. 3B through 3E illustrate a method of operating a mucosal resection device to perform a submucosal medical procedure to remove a desired region of the mucosal layer in a mammal according to an embodiment of the present invention. A first tissue guide 26 is positioned through the mucosal opening 50 to extend in the submucosal space beneath mucosal layer 42. The second tissue guide 28 is positioned above mucosal layer 42. As electrosurgical loop cutter wire 19 is energized and advanced, tissue guides 26 and 28 are brought closer together and cutter wire 19 cuts the tissue of mucosal layer 42 along the path defined by the slots. Once the movement of the cutter wire 19 stops, the supply of electrosurgical energy is halted. Cutter wire 19 is retracted to allow tissue guides 26 and 28 to open and the entire system is advanced forward to begin another cutting sequence. The number of cutting sequences required is dependant upon the size of the area to be resected, the length of the tissue guides and associated slots. This process may be used to completely remove certain sized lesions depending on the curvature of the tissue guides.

Figure 4A:
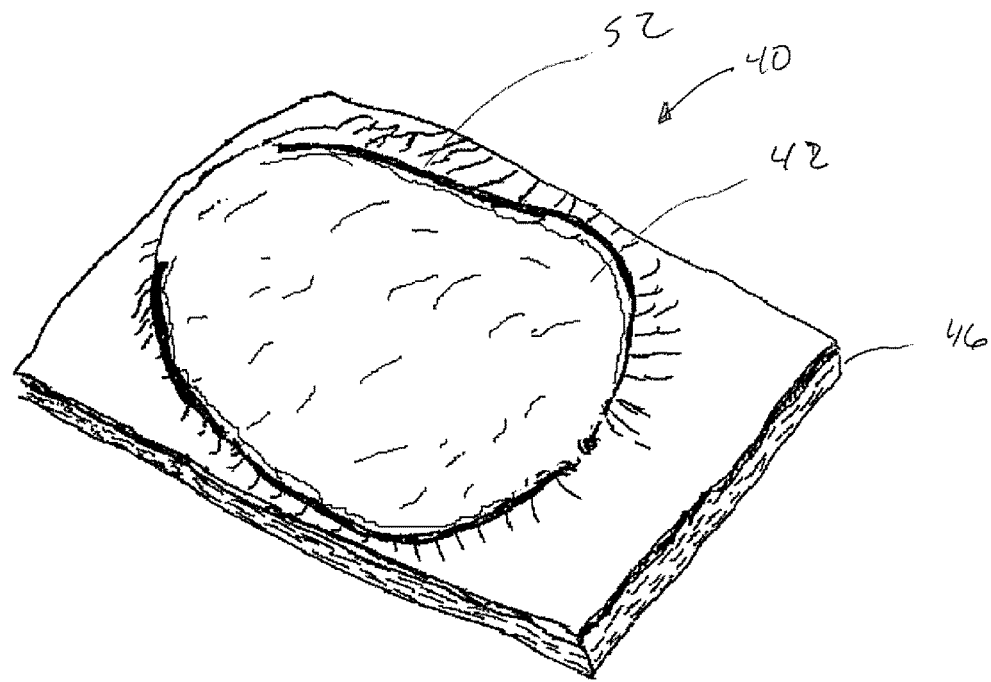
FIG. 4A is a perspective view showing a desired region of mucosal tissue which has been partially resected using the tissue resection device according to an embodiment of the present invention.
Figure 4B:
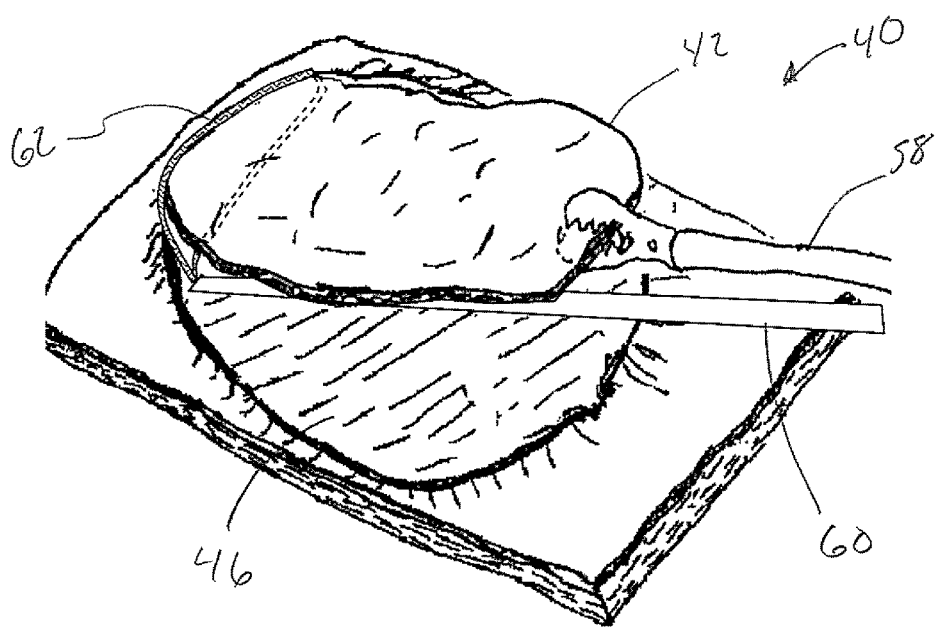

FIGS. 4A through 4C illustrate a partial resection of mucosal layer 42 using a tissue resection device of the present invention and subsequent method of complete removal using additional devices. The resultant cutting path 52 is show after multiple sequences using tissue resection device 10. The remaining dissected mucosal layer 42 may be manipulated using tissue grasper 58 and ensnared using an endoscopic snare 60. The loop 62 of the snare 60 is positioned around the remaining attached portion of mucosal layer 42. The snare may then be reduced in diameter and energized to complete the resection of mucosal layer 42.

Novel instruments, systems and methods have been disclosed to perform submucosal medical procedures in the digestive tract of a mammal. Although preferred embodiments of the invention have been described, it should be understood that various modifications including the substitution of elements or components which perform substantially the same function in the same way to achieve substantially the same result may be made by those skilled in the art without departing from the scope of the claims which follow.

What is claimed is:

1. An apparatus for resecting a target area of mucosal tissue comprising:
   an elongate member having proximal and distal sections wherein said distal section includes first and second guides, each a separate tube and each having a proximal end, a distal end, and a longitudinally extending slot along said guide and ending proximal of said distal end, at least one of said distal ends of said first and second guides having an outward bias relative to the other of said distal ends, and said slots defining a path; and
   a resection member having first and second proximal ends and a distal end wherein said first and second proximal ends extend within interiors of said first and second guides, respectively, and said distal end extends between said first and second guides of said elongate member such that said distal end of said resection member may traverse said path defined by said slots of said first and second guides,
   wherein distal advancement of said first and second proximal ends of said resection member within said first and second guides causes at least one of said first and second guides to be moved against said outward bias and be brought closer to the other of said first and second guides.

2. An apparatus according to claim 1, wherein said resection member is electro-conductive.

3. An apparatus according to claim 2, wherein said first and second guides are non-conductive and curved.

4. An apparatus according to claim 2, further comprising a proximal handle coupled to said proximal end of said elongate member and which longitudinally displaces said resection member through said distal section.

5. An apparatus according to claim 4, wherein said proximal handle includes an electrical connector adapted for coupling said resection member to an electrosurgical generator.

6. An apparatus according to claim 1, wherein said first and second guides are non-conductive.

7. An apparatus according to claim 6, wherein said first and second guides are curved.

8. An apparatus according to claim 7, wherein said slots face one another.

9. An apparatus according to claim 1, wherein said first and second guides are non-conductive, and said slots face one another.

10. An apparatus according to claim 1, wherein said slots face one another.

11. An apparatus according to claim 1, wherein when said resection member is retracted, said first and second guides are allowed to open apart from each other.

12. An apparatus according to claim 1, wherein proximal retraction of said resection member relative to the path allows said first and second guides to move away from each other under the force of said outward bias.

13. An apparatus according to claim 1, wherein said first and second proximal ends of said resection member each have an outer diameter that is larger than a width of the respective slot of said first and second guides.

14. An apparatus according to claim 1, wherein said first guide is longer than said second guide.

15. An apparatus for resecting a target area of mucosal tissue, comprising:
an elongate member having proximal and distal sections;
first and second electrically-insulated tubular guides coupled to said distal section, each of said guides defining a longitudinal slot, said longitudinal slots facing each other, each of said first and second guides having an outer diameter larger than a width of said longitudinal slots;
an electro-conductive resection member having proximal and distal ends wherein the distal end forms a loop that extends through said first guide, through said longitudinal slots, and back through said second guide,
wherein when said resection member is distally advanced relative to said first and second guides, said first and second guides are brought closer together, and when said resection member is retracted, said first and second guides are allowed to open apart from each other; and
a proximal handle coupled to said elongate member for longitudinally displacing said resection member within said longitudinal slots such that said resection member may traverse mucosal tissue along a path defined between said first and second guides and resect such mucosal tissue, said handle including an electrical connector adapted for coupling said resection member to an electrosurgical generator.

16. An apparatus according to claim 15, wherein said first and second guides have an arcuate shape.

17. An apparatus according to claim 15, wherein:
said tubular guides are configured in a 'Y'-configuration.

18. An apparatus for resecting a target area of mucosal tissue comprising:
an elongate member having proximal and distal sections wherein said distal section includes separate first and second tubular guides each having a proximal end, a distal end, and a longitudinally extending slot, and at least one of said distal ends of said first and second guides having an outward bias relative to the other of said distal ends, and said slots defining a path; and
a resection member having first and second proximal ends and a distal end wherein said first and second proximal ends extend within interiors of said first and second guides, respectively, and said distal end extends between said first and second guides of said elongate member such that said distal end of said resection member may traverse said path defined by said slots of said first and second guides, and said first and second proximal ends of said resection member each have an outer diameter that is larger than a width of the slot through the respective first and second guides,
wherein distal advancement of said first and second proximal ends of said resection member within said first and second guides causes at least one of said first and second guides to be moved against said outward bias and be brought closer to the other of said first and second guides.

* * * * *